US008258466B2

(12) United States Patent
Boyle et al.

(10) Patent No.: US 8,258,466 B2
(45) Date of Patent: *Sep. 4, 2012

(54) SMART FAIMS SENSOR

(75) Inventors: Paul Boyle, London (GB); Martyn Rush, Cambridge (GB); David Ruiz-Alonso, Cambridge (GB); Andrew H. Koehl, Cambridge (GB); Russell Parris, Cambridge (GB); Ashley Wilks, Cambridge (GB)

(73) Assignee: Owlstone Nanotech Inc, Cambridge (GB)

( * ) Notice: Subject to any disclaimer, the term of this patent is extended or adjusted under 35 U.S.C. 154(b) by 86 days.

This patent is subject to a terminal disclaimer.

(21) Appl. No.: 12/774,840

(22) Filed: May 6, 2010

(65) Prior Publication Data

US 2010/0213364 A1    Aug. 26, 2010

(51) Int. Cl.
  *H01J 49/00*  (2006.01)
  *B01D 59/44*  (2006.01)
(52) U.S. Cl. .......... 250/287; 250/281; 250/282
(58) Field of Classification Search .......... 250/281–293; 702/175, 182, 193
  See application file for complete search history.

(56) References Cited

U.S. PATENT DOCUMENTS

| | | | |
|---|---|---|---|
| 4,821,023 A | 4/1989 | Parks | |
| 6,495,823 B1 | 12/2002 | Miller et al. | |
| 6,512,224 B1 | 1/2003 | Miller et al. | |
| 6,806,463 B2 | 10/2004 | Miller et al. | |
| 7,005,632 B2 | 2/2006 | Miller et al. | |
| 2003/0084722 A1* | 5/2003 | Kim et al. | 73/504.08 |
| 2004/0047205 A1 | 3/2004 | Hazama et al. | |
| 2004/0094704 A1* | 5/2004 | Miller et al. | 250/287 |
| 2005/0045477 A1* | 3/2005 | Wei et al. | 204/431 |
| 2005/0145789 A1 | 7/2005 | Miller et al. | |
| 2005/0263699 A1 | 12/2005 | Miller et al. | |
| 2006/0054983 A1* | 3/2006 | Acar et al. | 257/415 |
| 2006/0055392 A1 | 3/2006 | Passmore et al. | |
| 2007/0001123 A1 | 1/2007 | Andrews et al. | |
| 2007/0158191 A1* | 7/2007 | Berger | 204/421 |
| 2008/0022755 A1* | 1/2008 | Shinbo et al. | 73/31.06 |
| 2008/0036444 A1* | 2/2008 | Paulus et al. | 324/71.1 |
| 2008/0143351 A1* | 6/2008 | Lee et al. | 324/698 |
| 2009/0051376 A1* | 2/2009 | Schnell et al. | 324/724 |

* cited by examiner

*Primary Examiner* — Phillip A Johnston
*Assistant Examiner* — Brooke Purinton
(74) *Attorney, Agent, or Firm* — Edwards Wildman Palmer LLP; Barry Kramer

(57) ABSTRACT

A smart FAIMS sensor system and method includes a 2/2-electrode filter that pumps the ions through the system and separates the ionic species, a detector for collecting the separated ions and generating a detector signal in response to the collected ions, and a controller configured to change the operating parameters of the system in response to changes in the sensor's environment detected by the sensor. The ability to dynamically change the operating parameters of the sensor enables the sensor to maintain high sensitivity to environmental threats while decreasing the incidences of false positive events.

14 Claims, 13 Drawing Sheets

Fig. 7a
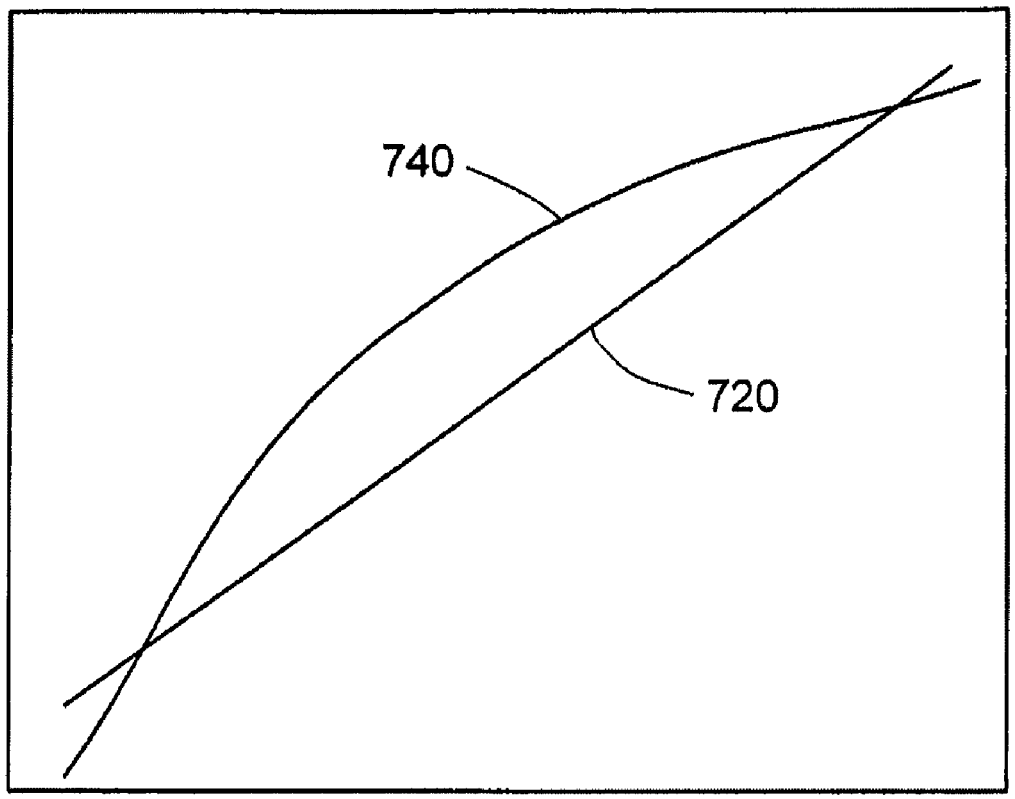
$V_L$
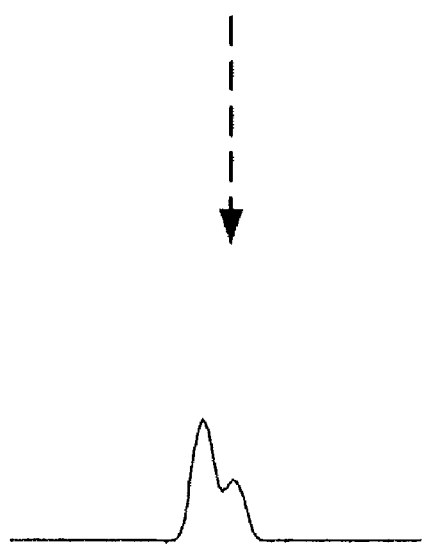
Fig. 7b
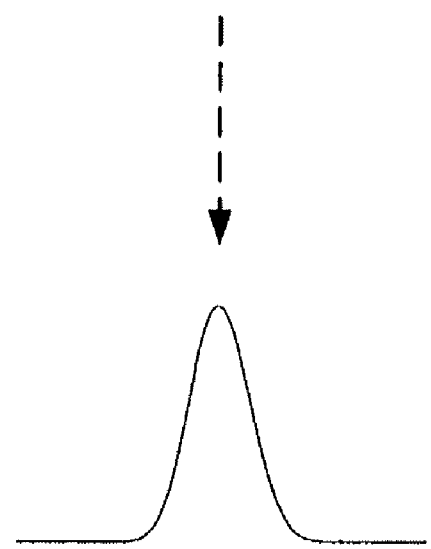
Fig. 7c

SMART FAIMS SENSOR

CROSS REFERENCE TO RELATED APPLICATIONS

This patent application claims the benefit of priority from U.S. patent application Ser. No. 11/489,989, filed Jul. 20, 2006, and issued as U.S. Pat. No. 7,714,277. The disclosure of the aforementioned patent is incorporated by reference herein in its entirety.

BACKGROUND

The present disclosure relates to chemical/biological environmental sensors. More specifically, the disclosure relates to systems and methods for smart FAIMS sensors that dynamically change their operating point in response to their environment.

Field Asymmetric Ion Mobility Spectroscopy (FAIMS) may be used to separate molecular or atomic ions based, in part, on the ions nonlinear ionic mobility in an electric field. In a typical FAIMS configuration, ions are directed between two plates that generate an electric field perpendicular to the flow direction of the ions. The electric field may be generated by applying a time varying voltage to the two plates. The time varying voltage is usually a superposition of two time varying signals or a superposition of a time varying signal and an adjustable constant signal.

A first component of the time varying signal is an asymmetric oscillation wherein the peak magnitude of, for example, the positive portion of the oscillation is different from the peak magnitude of the negative portion of the oscillation. The absolute value of the magnitude of the asymmetric signal is such that the electric field generated is usually greater than about 5,000 V/cm during the positive portion of the oscillation and less than about 1,000 V/cm during the negative portion of the oscillation cycle. In the example above, the durations of the positive and negative portions of the cycle may be adjusted such that the products of the electric field and the duration are approximately the same for both the positive and negative portions of the oscillation. In the example above, the duration of the negative portion of the oscillation cycle is preferably five times longer than the duration of the positive portion of the oscillation cycle.

If the ionic mobility of the ion is independent of the applied electric field, the ion will oscillate transversely to its direction of travel but will not drift transversely to its direction of travel. The ionic mobility, however, is usually not independent of the applied electric field and the ion will drift toward one of the electrodes and transversely to its direction of travel, the direction of the drift depending on whether the ionic mobility is an increasing or decreasing function of the applied electric field. If uncompensated, the ion will continue to drift toward one of the electrodes until it collides with the electrode.

A second voltage signal, $V_C$, may be superposed onto the oscillating signal to compensate the transverse drift of the ion. The transverse drift depends, inter alia, on the ion mass and the ion mobility, which are usually unique to each ionic species. By adjusting the second voltage signal to cancel the transverse drift of the ion, herein referred to as a compensation voltage, an operator of the device may select a particular ionic species. Alternatively, by sweeping the second voltage signal, the operator may obtain a spectrum of ionic species ordered by the combination of the species' mass and mobility.

Ions may be directed between the electrodes by a pump or by a second set of electrodes that generate an electric field in the direction of the ion's flow path. For example, U.S. Pat. Nos. 6,495,823 and 6,512,224 issued to Miller teach the use of a mechanical pump or a pair of electrodes to direct ions between the electrodes generating the transverse electric field. The use of a mechanical pump, however, has several disadvantages when FAIMS is used as a sensor. The mechanical pump usually adds significant bulk to the sensor and requires large power relative to the sensor. Furthermore, the time response of the mechanical pump significantly increases the time response of the FAIMS sensor. The electrical pump disclosed by Miller also adds to the bulk of the sensor system by the addition of the second pair of electrodes and its associated electronics.

SUMMARY OF THE DISCLOSURE

An exemplary smart FAIMS sensor system and method includes a 2/2-electrode filter that pumps the ions through the system and separates the ionic species, a detector for collecting the separated ions and generating a detector signal in response to the collected ions, and a controller configured to change the operating parameters of the system in response to changes in the sensor's environment detected by the sensor. The ability to dynamically change the operating parameters of the sensor enables the sensor to maintain high sensitivity to environmental threats while decreasing the incidences of false positive events.

One embodiment disclosed herein is directed to a method of operating a smart FAIMS sensor comprising: providing a FAIMS sensor comprising a filter for separating ionic species, the filter having a plurality of electrodes, each of the plurality of electrodes driven by a drive signal controlled by a controller and defining an operating point of the sensor, and a detector for collecting separated ionic species, the detector generating a detection signal in response to the collected ionic species; setting the operating point of the sensor to a first operating point; and setting the operating point of the sensor to a second operating point based on the detection signal. In a further aspect, an alarm is registered when the detection signal generated at the second operating point exceeds a predetermined threshold associated with the second operating point. In another aspect, the second operating point is set when the detection signal generated at the first operating point exceeds a predetermined threshold associated with the first operating point. In another aspect, the operating point of the sensor is set by changing a drive voltage. In another aspect, the operating point of the sensor is set by changing a pulse height of an asymmetric oscillating signal applied to the plurality of electrodes. In another aspect, the first operating point corresponds to a high sensitivity operating mode. In another aspect, the second operating point corresponds to a high selectivity operating mode. In another aspect, the first operating point is set according to a threat condition in a deployed environment.

Another embodiment in accordance with the disclosure is directed to a smart FAIMS sensor comprising: a filter having a 2/2 electrode configured to separate ions according to a plurality of signals applied to the 2/2 electrode, the plurality of signals defining an operating point of the sensor; a detector configured to capture the separated ions and generate a detection signal based on the captured ions; and a controller configured to change the operating point of the sensor based on the detection signal. In a further aspect, a communication module is configured to receive commands from the controller and to transmit the detection signal to the controller. In another aspect, the communication module is a wireless transmitter/receiver. In a further aspect, the 2/2 electrode further comprises a first and second electrode, each of the first and second electrode having a first and second contact pad disposed on opposite faces of each of the first and second electrode, each contact pad receiving one of the plurality of signals. In a further aspect, the difference between the one of a plurality of signals applied to the first contact pad and the one of a plurality of signals applied to the second contact pad is a longitudinal drive voltage that pumps the separated ions through the filter.

Another embodiment in accordance with the present disclosure is directed to a method of operating a FAIMS sensor comprising: providing a FAIMS sensor, the sensor characterized by one or more operating parameters, the set of the one or more operating parameters defining an operating mode; placing the sensor into a first operating mode, the first operating mode characterized by a high sensitivity to a target species; dynamically switching to a second operating mode when the target species is detected at the first operating mode; and registering an alarm when the target species is detected at the second operating mode. In a further aspect, the second operating mode is characterized by a lower sensitivity to the target species relative to the first operating mode and further characterized by a higher selectivity to the target species relative to the first operating mode. In another aspect, the one or more operating parameters include a drive voltage, the drive voltage controlling an ion flow rate through a filter in the sensor. In another aspect, the step of dynamically switching comprises reducing the drive voltage. In another aspect, the one or more operating parameters include a pulse height, the pulse height determining an amplitude of an asymmetric oscillating field generated in a filter in the sensor. In another aspect, the step of dynamically switching comprises increasing the pulse height.

BRIEF DESCRIPTION OF THE DRAWINGS

Embodiments of the invention will be described by reference to the preferred and alternative embodiments thereof in conjunction with the drawings in which:

FIG. 7a is an illustrative graph of the ion transmission factor and the full width at half maximum (FWHM) as a function of drive voltage, $V_L$;

FIG. 7b is an illustrative scan at a low flow rate;

FIG. 7c is an illustrative scan at a high flow rate;

DETAILED DESCRIPTION

Preferred embodiments of the present invention include a FAIMS system such as the one described in PCT application numbers PCT/GB2005/050124 and PCT/GB2005/050126, referred to collectively as "Owlstone" systems and herein incorporated by reference in their entirety.

Figure 1:
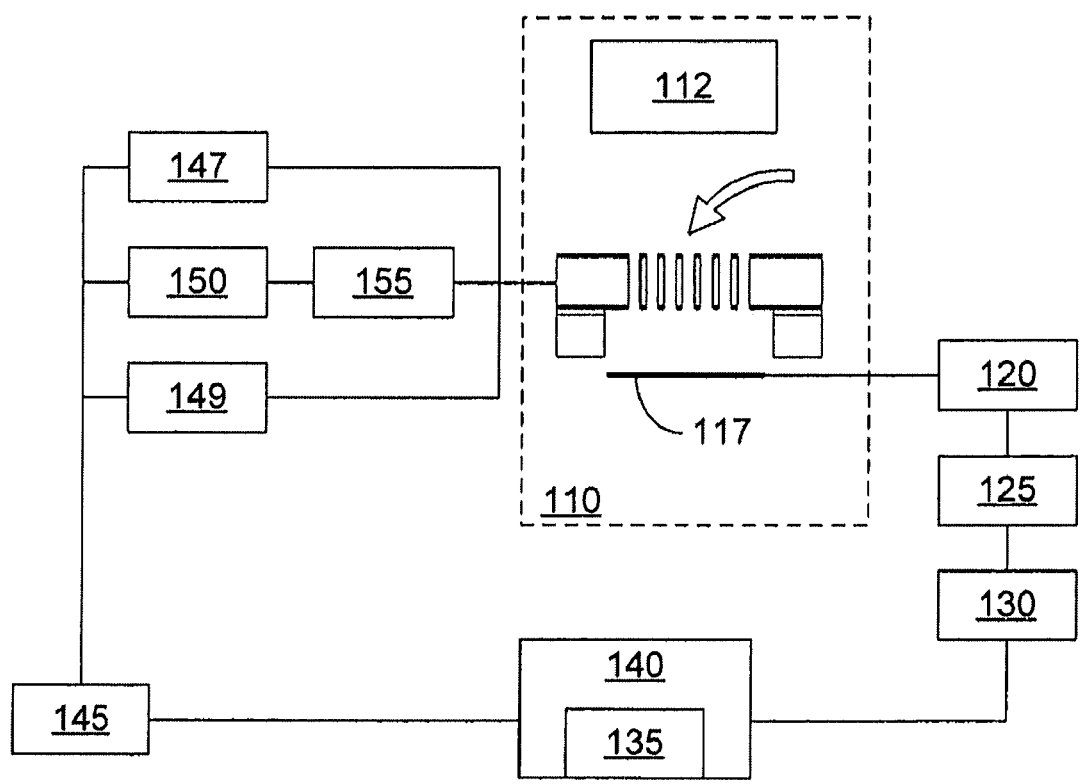
FIG. 1 is a block diagram of an embodiment of the present invention.

FIG. 1 is a block diagram of a smart FAIMS sensor 100 in one embodiment of the present invention. Sampling module 110 includes an ionization source 112 for ionizing molecules drawn into the sampling module and a filter 115 for separating the ions according to their mass and ionic mobility. Filtered ions are collected with a detection electrode 117. A low current amplifier 120, such as a transimpedance amplifier, for example, amplifies the signal from the detection electrode 117 and provides an amplified signal representing the detected ion current to an output DAQ 125. Additional signal processing may be performed on the amplified signal with a signal processing module 130.

A control module 140 receives the processed signal from the signal processing module 130 and can change one or more operating parameters of the sensor 100 based on the received signal. Control module 140 may include a communication module 135 that receives instructions for the control module 140 and transmits alarms or sensor status information to a central station. In some embodiments, the control module 140 may be incorporated as part of the sensor package. In other embodiments, the control module 140 may be a wireless transmitter/receiver configured to transmit the signal from the signal processing module and receive commands from a remote control module. Removing the control module from the sensor package reduces the cost and power requirements of the sensor 100 enabling the deployment of many such sensors over a wide area.

Filter 115 is preferably a 2/2-electrode filter that generates an asymmetric oscillating electric field and a compensation field that are both transverse to the ion's direction of travel through the filter. The convention used herein to describe the filter uses two numbers that represent the number of electrodes and the number of contact pads per electrode separated by the "/". A 2/2-electrode filter, therefore, describes a two-electrode configuration with each electrode having two contact pads. The use of more than one contact pad per electrode enables independent control of the transverse and longitudinal fields generated by the 2/2-electrode filter. In a preferred embodiment, the 2/2-electrode filter may also generate a longitudinal drive field that pumps ions through the filter 115. The asymmetric oscillating electric field is generated by applying appropriate voltage signals to each of the four contact pads of the filter. The asymmetric voltage signal is generated by an asymmetric pulse generator 150 and amplified with a high voltage amplifier 155. The pulse width, repetition rate, and amplitude of the asymmetric voltage signal are set by the control module 140 through an electronic input interface 145. The transverse compensation field is generated by applying an appropriate compensation voltage signal to each of the contact pads in the filter. A voltage source 157 generates the compensation voltage signal with the amplitude and sweep rate of the compensation voltage signal controlled by the control module 140 through the electronic input interface 145. A power supply provides the necessary power to each of the components shown in FIG. 1. The longitudinal drive field is generated by applying an appropriate drive voltage signal to each of the contact pads in the filer. A drive voltage source 149 generates the DC drive voltage signal with the voltage drop controlled by the control module through the electronic input interface 145.

Figure 2:
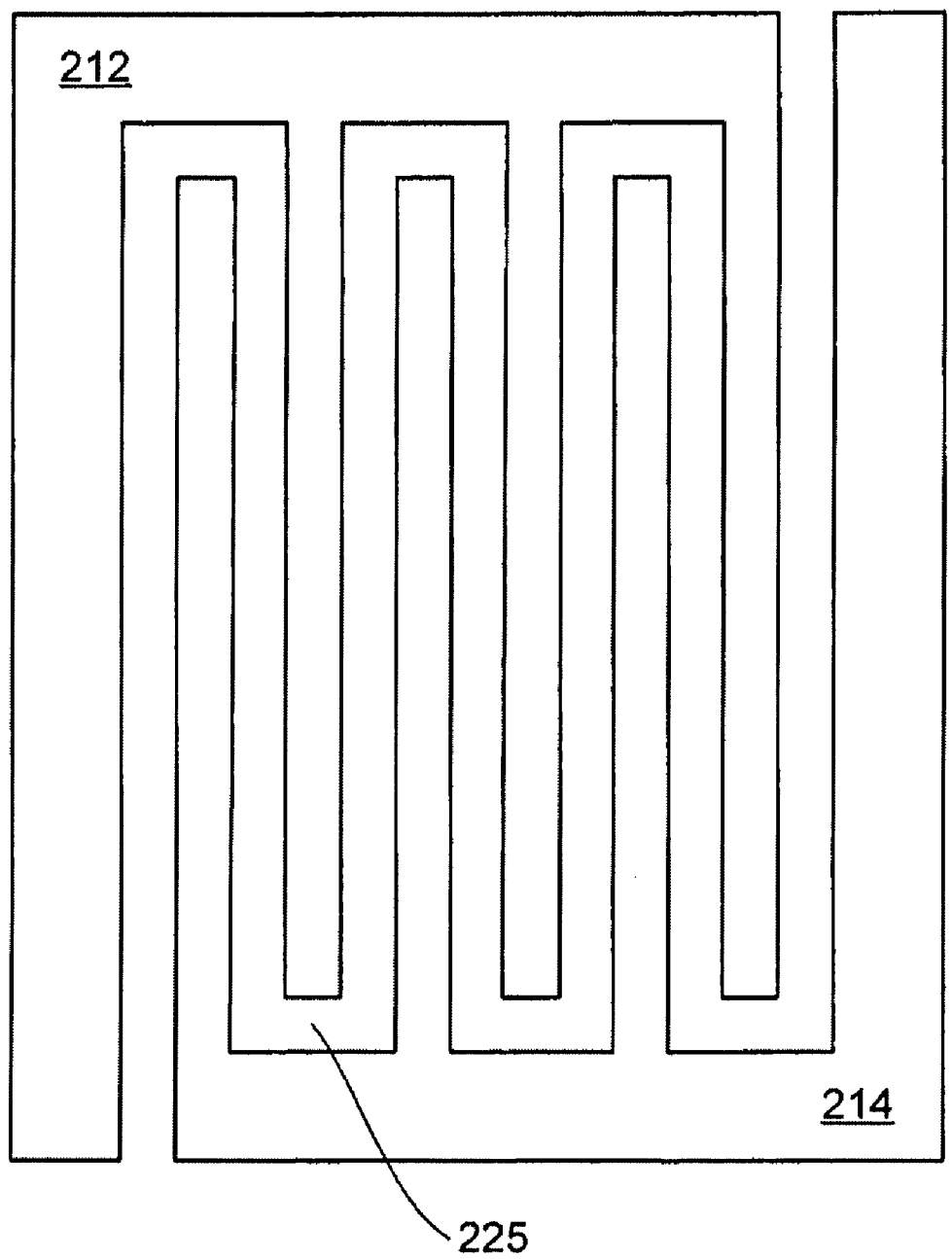
FIG. 2 is a top view of the filter shown in FIG. 1.

FIG. 2 is a top view of the 2/2-electrode filter shown in FIG. 1. The filter includes two interdigitated comb electrodes 212, 214. Each comb electrode 212, 214 supports a contact pad on its top surface and a second contact pad on its bottom surface.

The spacing between the comb structures 212, 214 is preferably between 1 mm and 1 µm and most preferably between 100 µm and 10 µm. Large electric fields may be generated with the application of modest voltage potentials applied across the narrow gap between the fingers of the comb. The interdigitated configuration allows for a large cross-sectional flow area 225 while keeping the narrow gap between the comb fingers. The large cross-sectional flow area increases the number of ions passing through the filter and increases the signal strength of the detected ions. The increased signal strength of the detected ions reduces the rate of erroneous detection events and increases sensitivity.

Figure 3:
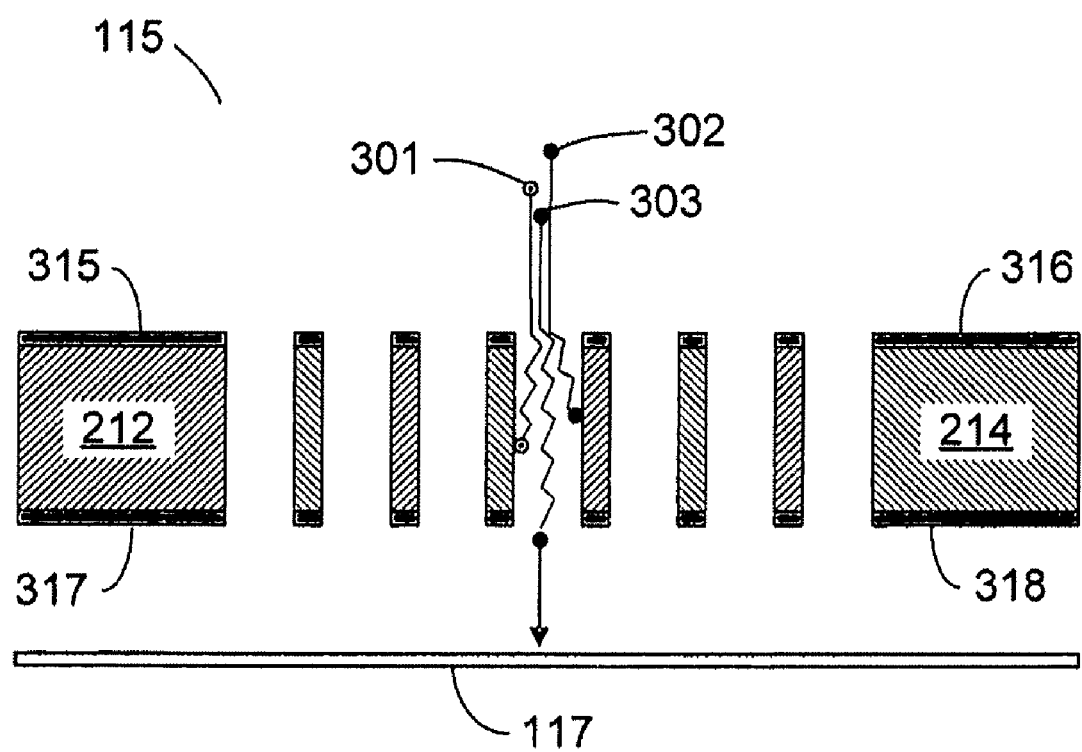
FIG. 3 is a cross-section view of the filter shown in FIG. 1.

FIG. 3 is a cross-sectional view of the filter shown in FIG. 2. In FIG. 3, a filter 115 separates ion species 301, 302, 303 according to each ion species' ionic mobility and mass. The filtered ions are collected at a detector electrode 117. The filter 115 includes two interdigitated comb structures 212, 214. A contact pad 315, 316, 317, 318 is disposed on the top and bottom surfaces of each comb electrode to create a 2/2-electrode filter. The comb structure 212, 214 provides mechanical support and separation for the filter contact pads and may be of any high resistivity material such as, for example, high resistivity silicon. The comb structure is preferably manufactured using methods typically used for Micro-Electro-Mechanical Systems (MEMS) such as, for example, Deep Reactive Ion Etching (DRIE).

In FIG. 3, paths of ion species are indicated and show that the ions oscillate transversely to their flow direction through the filter in response to the transverse asymmetric oscillation field generated by contact pads 315, 316, 317, and 318. Each ion species reacts differently to the asymmetric field according to the ion's electric mobility and mass. The transverse compensation field selects an ionic species 303 by compensating for the transverse drift arising from the nonlinear behavior of electric mobility as a function of electric field for that ionic species. The selected ions 303 are collected by detector electrode 117, which generates a current that is proportional to the number of ions collected by the electrode 117. Other ionic species that have different electric mobilities eventually collide with one of the comb structures 212, 214.

Figure 4:
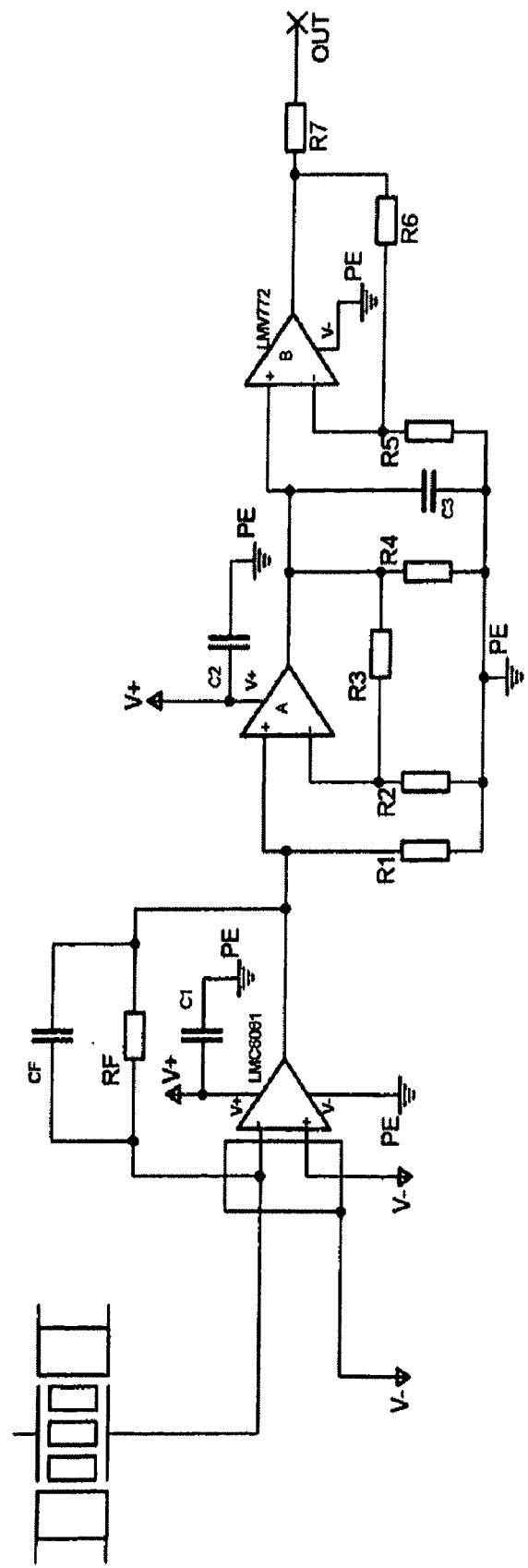
FIG. 4 is a circuit diagram for a low current amplifier used in some embodiments of the present invention.
Figure 5:
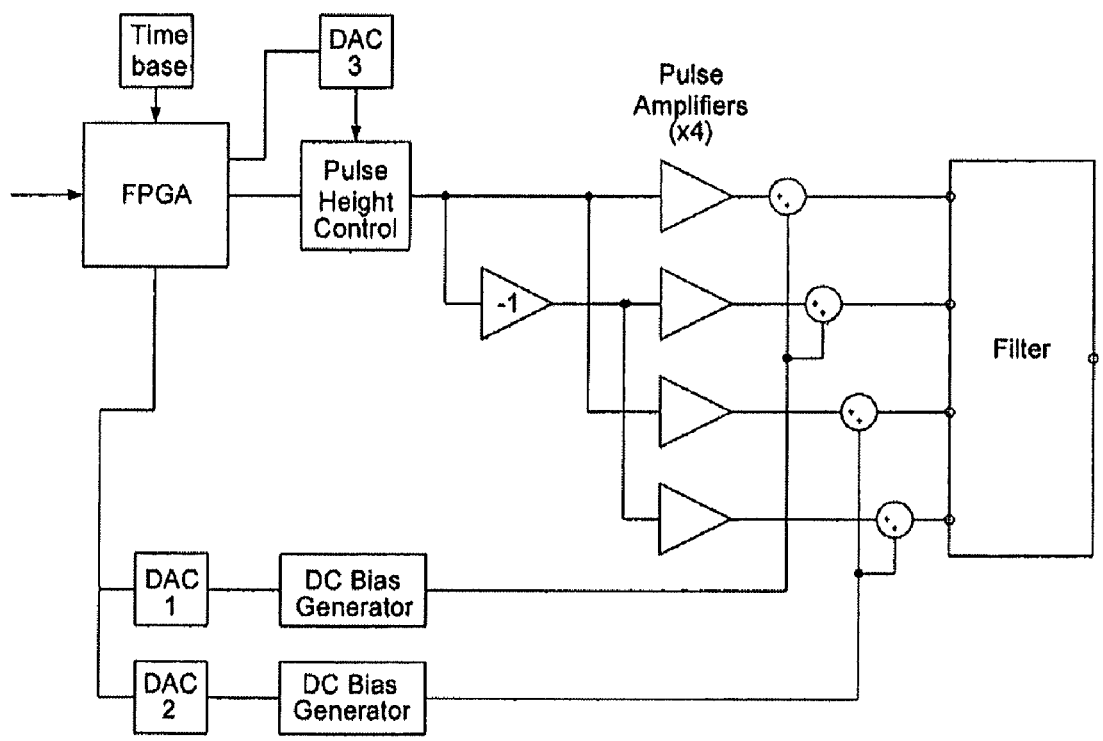
FIG. 5 is a diagram of the electrode drive circuit used in some embodiments of the present invention.

FIG. 4 is a diagram for a low current amplifier used in some embodiments of the present invention. The circuit shown in FIG. 4 shows a transimpedence amplifier but one of skill in the art should understand that other types of amplifiers may be used and are within the scope of the present invention. FIG. 5 is a diagram illustrating the electrode drive circuitry used in some embodiments of the present invention.

Figure 6:
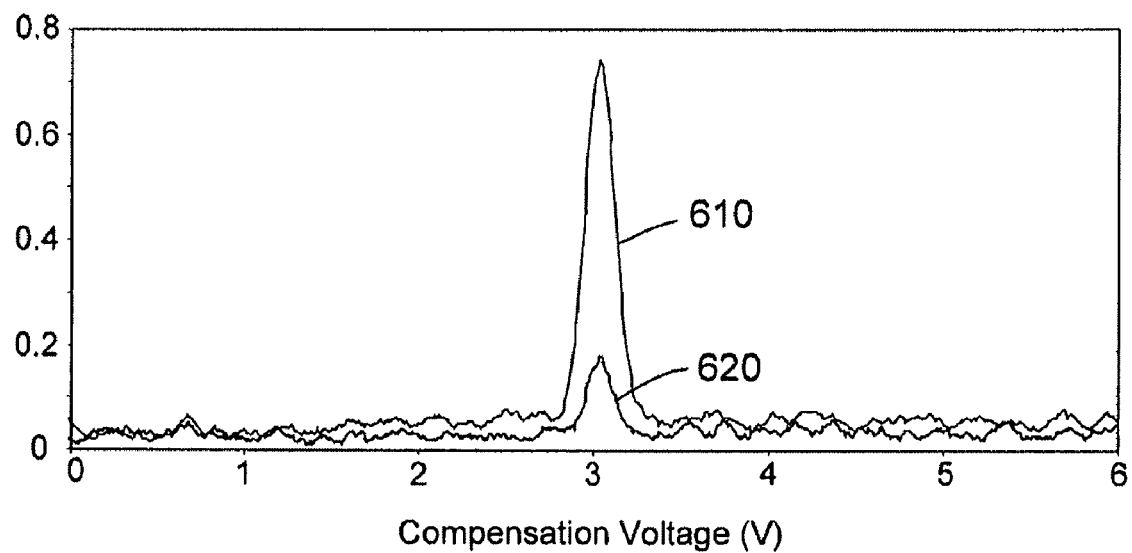
FIG. 6 is an illustrative plot of the ion current as a function of compensation voltage at two flow rates.

FIG. 6 is an illustrative plot of ion current as a function of compensation voltage, $V_C$ for a single analyte at two flow rates. The ion current represents the current generated by the ions passing through the filter and collected by the detector electrode. In FIG. 6, an upper curve 610 represents a high flow rate scan and the lower curve 620 represents a lower flow rate scan. Each curve shows a peak around 3V corresponding to the single target analyte but the height and width of the peaks differ. The high flow rate scan exhibits a larger and wider peak than the low flow rate scan.

A larger peak produces a larger signal-to-noise ratio, which gives greater confidence that the target analyte has been correctly detected and is not due to a random noise fluctuation. A smaller signal-to-noise ratio, as illustrated in the low flow rate plot can increase the incidences of false positives where the lower peak height is difficult to distinguish from the amplitudes of a noise fluctuation. In many instances, a false positive may have little or minor harmful consequences but in other situations, a false positive may generate an unwanted cost. Therefore, reducing the false positive rate of a sensor is usually preferred. In this instance, a high flow rate may be preferred to reduce the false positive rate.

A high flow rate, however, also tends to broaden the peak, which reduces the selectivity of the sensor. A broader peak decreases the ability of the sensor to distinguish between two different ionic species, in other words, the selectivity of the sensor is reduced. High selectivity is desired to distinguish a target species from other benign species that may be present in environment of the sensor. If a target species is close to a benign environmental species, a scan may show a single broad peak instead of two closely spaced peaks with one peak representing the target species and the second peak representing the benign species. In such a situation, the sensor cannot determine if the detected peak is only the expected benign species or if the broad detected peak includes the target species. If the sensor is configured to raise an alarm when a broad peak is detected, the false positive rate increases. If, on the other hand, the sensor raises an alarm only when two distinct peaks are detected, the sensor may fail to raise an alarm when the target species is actually present. Therefore, increasing the flow rate through the FAIMS sensor increases the signal-to-noise ratio of a detected peak but decreases the selectivity of the FAIMS sensor.

FIG. 7a is an illustrative graph of the ion transmission factor 740 and the full width at half maximum (FWHM) 720 as a function of drive voltage, $V_L$. The drive voltage, $V_L$, is preferably a DC voltage applied across the top 315, 316 and bottom 317, 318 contact pads of the filter that acts to drive, or pump, the ions through the filter. Increasing $V_L$ increases the ion flow rate through the filter. The peak height is approximately proportional to the product of the ion transmission factor and drive voltage. In FIG. 7a, plot 720 illustrates the width of a peak representing an ionic species increases monotonically with the drive voltage. FIG. 7b is an illustrative scan at a low flow rate. In FIG. 7b, the scan plots the ion current as a function of compensation voltage. In FIG. 7b, plot 740 illustrates the peak height increasing nonlinearly as the drive voltage increases. FIG. 7b is an illustrative graph of the ion current as a function of the compensation voltage at a low flow rate, represented by a low $V_L$. FIG. 7c is an illustrative scan at a high flow rate. The ion current indicates two peaks closely spaced with both peaks being smaller than the single peak shown in FIG. 7c. The single peak in FIG. 7c, however, cannot distinguish the two analytes shown in FIG. 7b because the width of the peak shown in FIG. 7c is much broader than the width of the peaks shown in FIG. 7b.

An operator of the FAIMS sensor may set an operating point of the device by setting an operating parameter such as, for example, the drive voltage to a desired value. If high selectivity is desired, a small drive voltage may be selected. Conversely, if high sensitivity is desired, a large drive voltage may be selected. The antagonistic relation between sensitivity and selectivity on drive voltage, however, prevents the use of drive voltage to set the operating point of the device such that sensitivity and selectivity are both maximized. The ability to change the drive voltage, however, enables the operator of the FAIMS sensor to program a controller to dynamically change the operating point of the device in response to detected changes in the environment.

Figure 8:
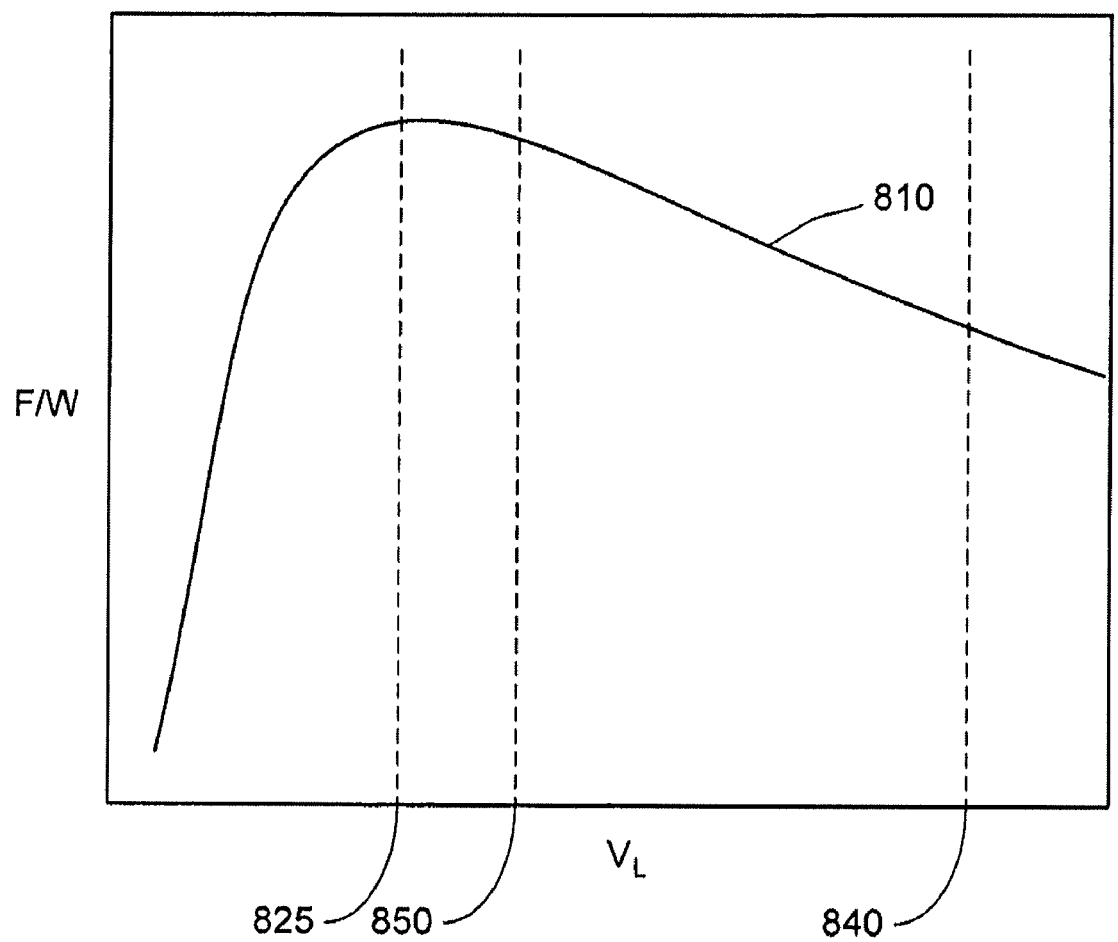
FIG. 8 is an illustrative plot of the ratio of the ion transmission factor and FWHM as a function of drive voltage, $V_L$.

FIG. 8 is an illustrative plot of the ratio of the ion transmission factor and FWHM as a function of drive voltage, $V_L$. The curve 810 exhibits a maximum at voltage point 825 where the device exhibits a combination of high signal (sensitivity) and narrow width (high selectivity). If the drive voltage is increased above 825, sensitivity increases but at the expense of lower selectivity. Conversely, if the voltage is decreased below 825, selectivity increases but at the expense of sensitivity. In many situations, the drive voltage may be set to a voltage value corresponding to point 825. In other situations, it may be very important to detect the target species as early as possible. In such a situation, the operating point may be set to a value indicated by point 840 in FIG. 8 where the device is very sensitive to small concentrations of the target species. If the sensor detects a possible presence of the target species, the controller may be configured to change dynamically the operating point of the device to, for example, point 850 in FIG. 8. At point 850, the sensitivity of the device is reduced but the selectivity increases, which should reduce the rate of false positive detections. If the sensor still detects a response at point 850, an alarm is sent to the central station. If, on the other hand, the sensor does not detect a response at point 850, the initial event detection at 840 is probably a false positive signal and not alarm is sent.

Figure 9:
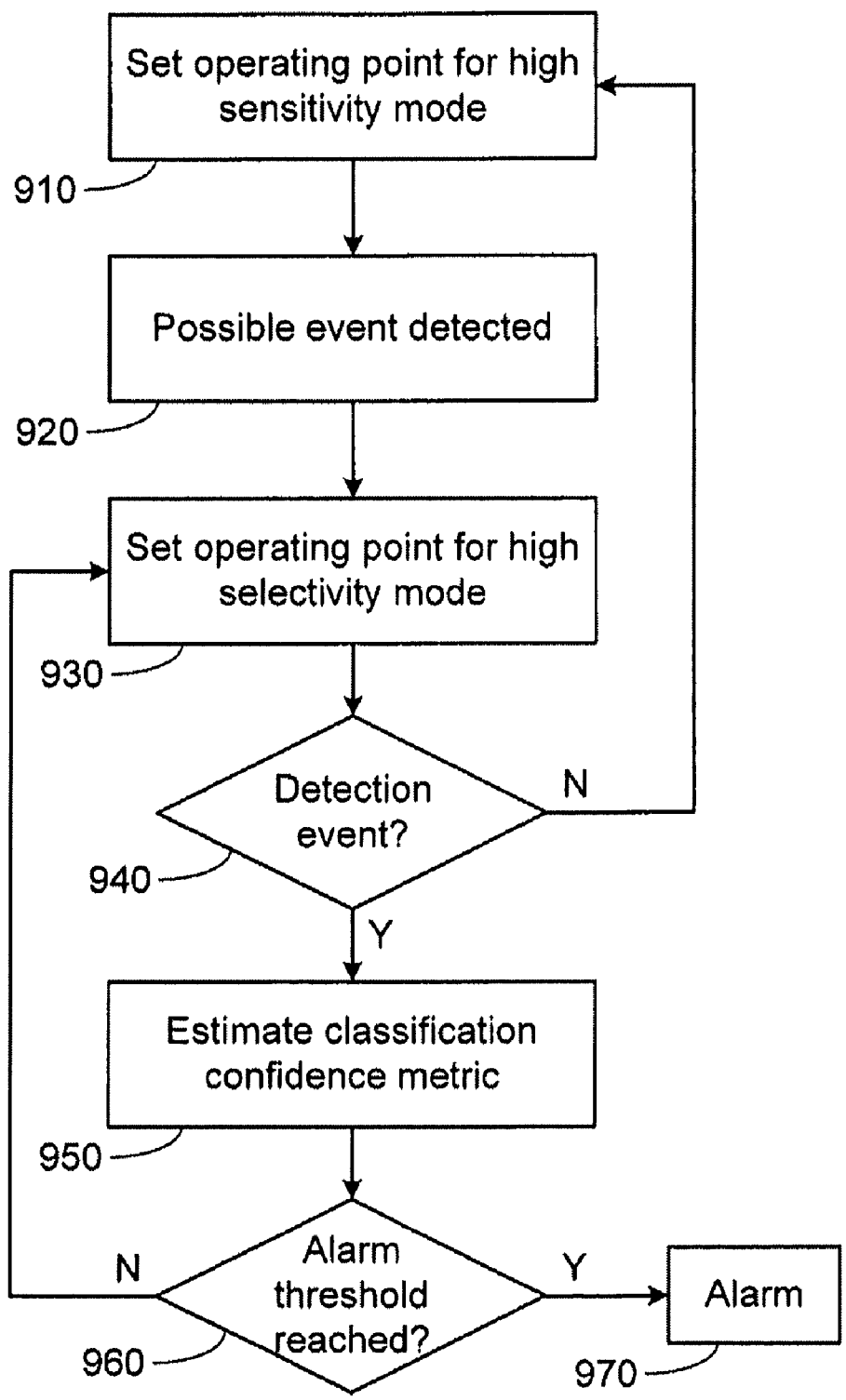
FIG. 9 is a flow chart illustrating a process used in some embodiments of the present invention.

FIG. 9 is a flow chart illustrating a process used in some embodiments of the present invention. In FIG. 9, the device is initially configured to operate in a high sensitivity mode at step 910. A high sensitivity mode may be selected when, for example, the possible presence of the target analyte is considered high. In step 910, the control module sets one or more operating parameters of the sensor to place the sensor in a high sensitivity mode. For example, the control module may set the drive voltage to a high value to increase the ion flow through the filter.

The sensor operates in the high sensitivity mode until step 920 when a possible event is detected. The occurrence of an event may be detected based on one or more predetermined threshold values. For example, if the ion current at a predetermined compensation voltage corresponding to a target analyte rises above an event threshold value, the control module may classify the occurrence as an event. At step 930, the control module changes the operating parameters of the sensor to increase the selectivity of the sensor by, for example, decreasing the drive voltage. The control module may also adjust other operating parameters such as sample time, peak RF voltage, or the scan range of the compensation voltage to assist in detecting a second event while in the high selectivity operating mode. At 940, the processed signal is compared to a second predetermined threshold value and an event is declared if the processed signal exceeds the second predetermined threshold value. If a second event is not detected in the high selectivity-operating mode, the control module classifies the event as a false positive event, jumps back to step 910, and changes the operating parameters of the sensor to the high sensitivity-operating mode.

If a second event is detected at step 940, a classification confidence statistic is estimated using Bayesian classification algorithms. By changing the operating point of the sensor, the confidence statistic can be increased. For example, the initial high sensitivity mode event may produce a confidence statistic of less than 95% likelihood that the analyte is present. By changing the operating point of the sensor to a high selectivity mode, the confidence statistic may be increased to greater than 95% and preferably greater than 99% likelihood that the analyte is present.

In step 960, the event is compared to one or more predetermined alarm criteria and if the alarm criteria are met, an alarm is set in step 970. If the event does not met the alarm criteria, the control module jumps back to step 930 and repeats the high selectivity measurement. An example of an alarm criterion is greater than 95% likelihood that the analyte is present. The alarm confidence level may be selected by balancing the cost of a false alarm against the cost of not detecting the analyte when it is actually present. For example, if the target analyte is a toxin that could result in death, the confidence level may be set to a lower value such as, for example, 90% to increase the probability that an alarm is initiated if the toxin is present. If, on the other hand, the target analyte is merely a nuisance but the cost of an evacuation is large, the confidence level may be to a higher value such as, for example, 99% to reduce the incidences of false positive events that require an evacuation.

Figure 10:
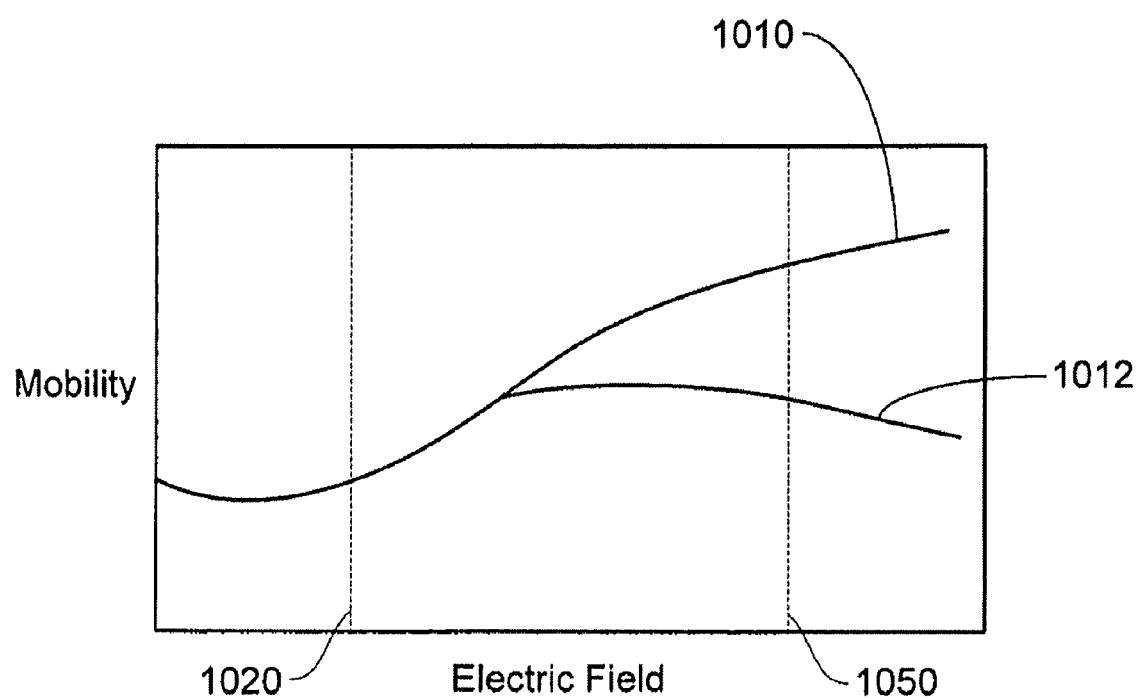
FIG. 10 is an exemplar plot illustrating the dependence of mobility of two ionic species.

In some embodiments, a second operating parameter may be adjusted to change dynamically the operating point of the sensor. An example of such an operating parameter is the pulse height of the transverse oscillating field. FIG. 10 is an exemplar plot illustrating the dependence of mobility of 2 ionic species, 1010 and 1012, as a function of electric field. FIG. 10 shows that at low field strengths, indicated by point 1020, the mobilities of the two species are very close to each other. In such a situation, the filter would not be able to separate efficiently the two species. As the field strength increases to, for example, point 1050, the difference in the mobilities of the two species increases, thereby increasing the ability of the filter to separate the two species. In other words, the selectivity of the filter may be increased by increasing the pulse height of the transverse oscillating field.

Figure 11:
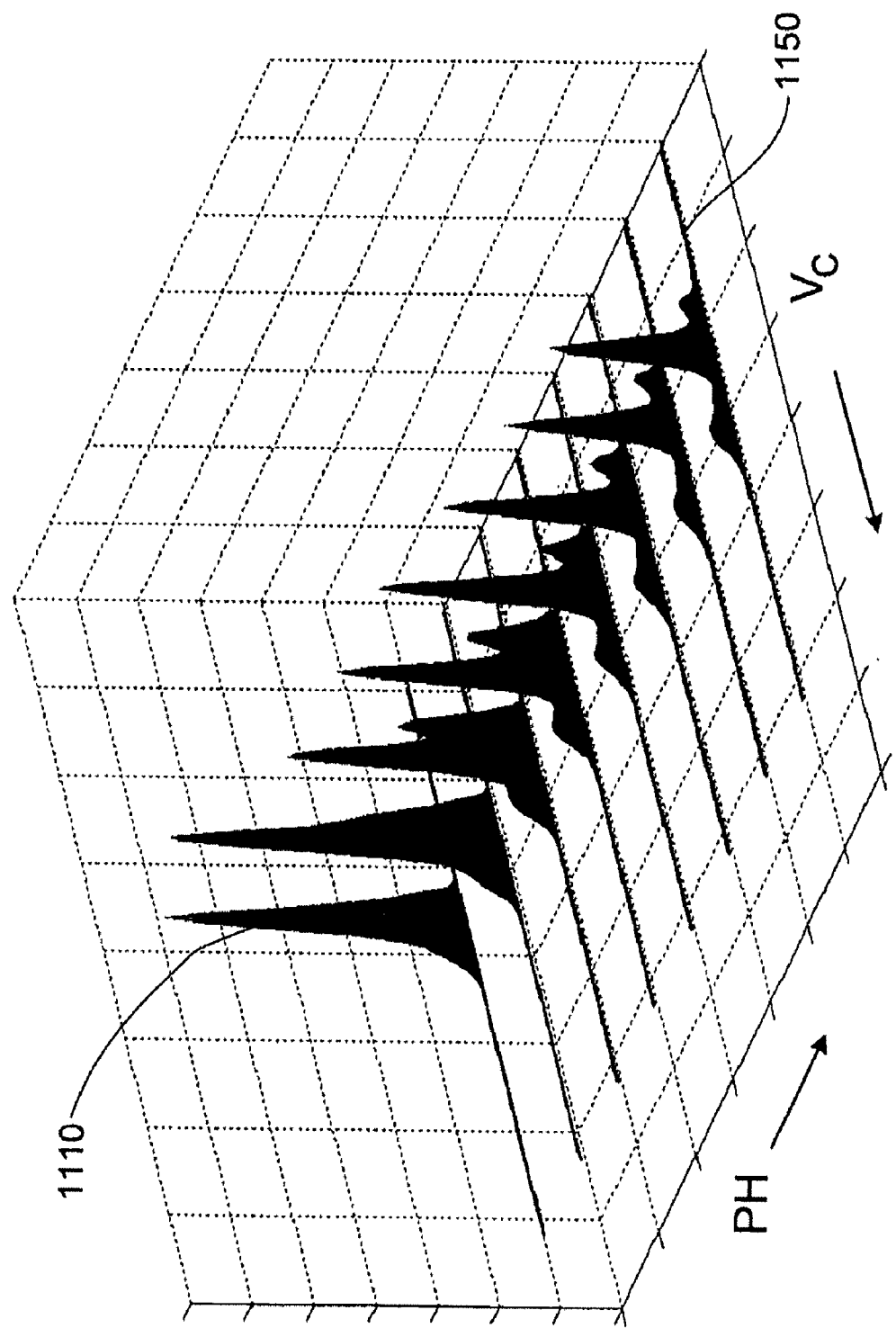
FIG. 11 shows several scans as a function of peak pulse height.

FIG. 11 shows several scans as a function of peak pulse height. Each scan plots the ion current as a function of compensation voltage. The arrows along the compensation voltage (Vc) and pulse height (PH) axes indicate the direction of increasing magnitude of the associated variable. Scan 1110, using a relatively small pulse height, indicates a single, large peak. Scan 1150, using a relatively large pulse height, indicates three peaks instead of the single peak of scan 1110.

In some embodiments, both the drive voltage and the pulse height may be adjusted to increase both sensitivity and selectivity of the sensor simultaneously. Increasing the drive voltage increases the ion flow through the sensor and increases the sensitivity of the sensor. Increasing the pulse height increases the ion mobility differences between species and increases the selectivity of the device. Selection of the pulse height depends on the target species and the environmental species that are expected to be present during deployment of the sensor. The pulse height may be selected to maximize the selectivity of the target species from the expected environmental species.

The sensor described in the Owlstone applications are very compact and inexpensive to fabricate compared to the original benchtop-sized FAIMS device. The filter disclosed in the Owlstone applications referenced above may be less than 10 $cm^2$ in surface area and are preferably less than 5 $cm^2$ in surface area. The small size of the filter enables the packaging of more than one filter in a housing that is less than about 0.5 L. The use of multiple sensors in a sensor array can increase selectivity and reduce the false positive rate of the device.

Figure 12:
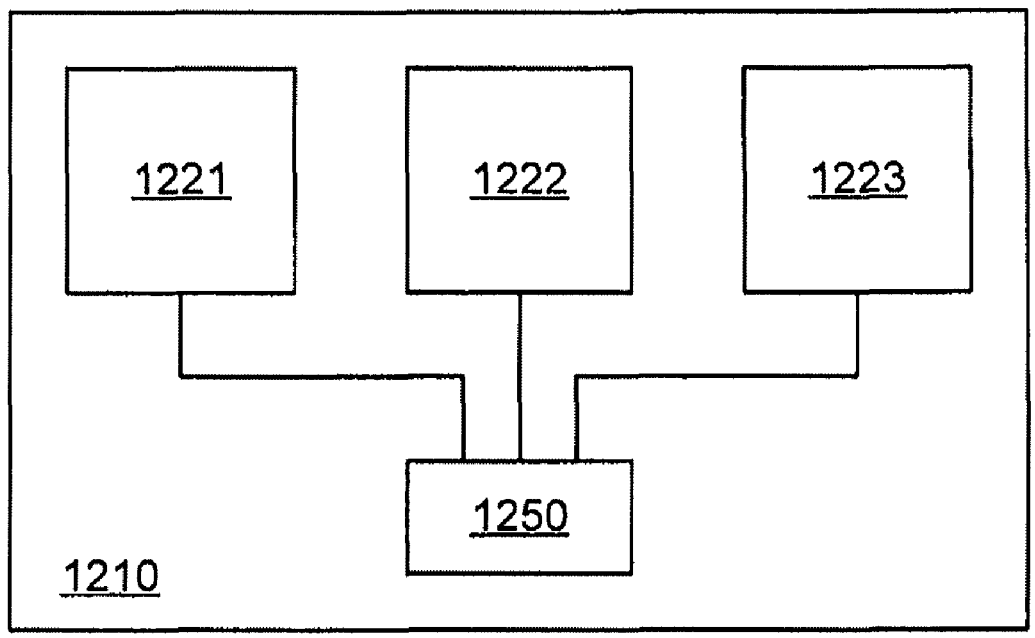
FIG. 12 is a block diagram of an embodiment of the present invention illustrating a sensor array.
Figure 12:
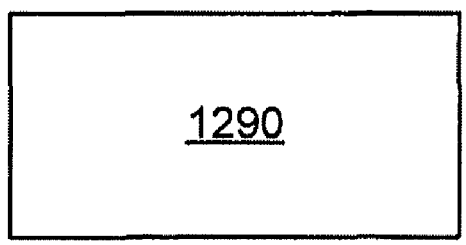

FIG. 12 is a block diagram of an embodiment of the present invention illustrating a sensor array. In the embodiment shown in FIG. 12, sensors 1221, 1222, 1223 are shown housed in a common package 1210. Each sensor is configured to communicate with a central controller 1290 through a wireless transmitter/receiver 1250. Although three sensors are shown in FIG. 12, the package may house any number of sensors according to the desired size of the housing. Each sensor preferably includes its own filter, electronics to drive the filter electrodes, detector, detector electronics, and the appropriate interface electronics to send data to, and receive commands from, the central controller 1290. A wireless central controller 1290 enables the sensor array to be updated after deployment in the field by, for example, changing the operating conditions of the sensor array to detect new chemical species or reflect a change in the threat environment.

Each sensor shown in FIG. 12 may be set to a different operating point and have a different threshold criterion for sending an alarm. In a preferred embodiment, an alarm is registered only when each sensor has exceeded its threshold criterion. It is believed that an interferant species such as a benign environmental species, for example, is unlikely to have the same signature as the target species at every operating point and registering an alarm only when each threshold criterion is exceeded for their respective sensors further reduces the probability that a registered alarm is a false alarm.

If the sensor array does not have access to an external power source and must use a portable power source such as, for example, a battery, the deployed lifetime of the sensor may be extended by turning on each sensor only when required. The battery life is extended because it does not have to continually power each sensor in the array but turns on each sensor only when necessary. For example, a first sensor in the sensor array may have its operating point set to a high sensitivity mode. During deployment, only the first sensor operates until it detects a possible event. When the first sensor detects a possible event by exceeding a first threshold criterion, for example, a second sensor is activated. The second sensor is set to a different operating point from the first sensor, preferably to an operating mode that has a higher selectivity than the first sensor. If a second threshold criterion associated with the second sensor is exceeded, a third sensor operating at a third operating point and having a third threshold criterion is activated. If the second threshold criterion is not exceeded, the event is probably a false signal, the second sensor is deactivated, and the first sensor is reset to continue monitoring its environment. The sequential activation of sensors in a cascading series of, for example, increasing sensitivity continues until all sensors in the array have been activated. An alarm is registered only when each sensor in the array has exceeded its respective threshold criterion.

Figure 13:
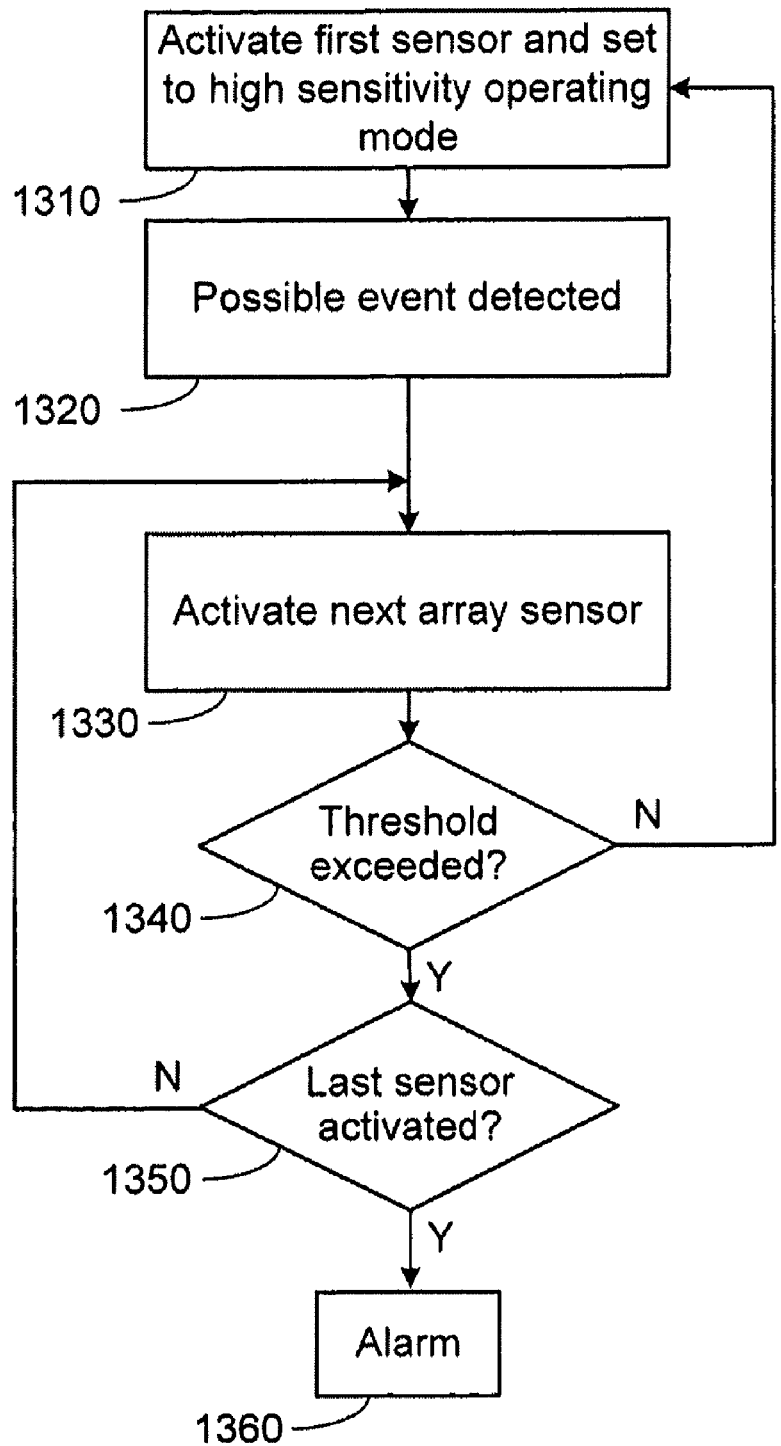
FIG. 13 is a flow diagram illustrating an embodiment of the present invention.

FIG. 13 is a flow diagram illustrating an embodiment of the present invention. In FIG. 13, a sensor array is initialized at step 1310 by setting the operating point of the first sensor to a high-sensitivity operating mode. The high-sensitivity operating mode may be set by setting the drive voltage to a relatively high value to pump more ions through the filter, thereby increasing the sensitivity of the sensor. The drive voltage may be set to a relatively high value if the threat environment is high. If the threat environment is low, the drive voltage may be set to a lower value than the value used in the high threat environment. The remaining sensors in the sensor array are preferably put into a deactivated state to prolong battery life of the sensor array. In step 1320, a possible event is detected when a predetermined threshold value associated with the first sensor's operating point is exceeded.

When a possible event is detected, the controller activates a next sensor in a sensor array at step 1330. The next sensor is set to a predetermined operating point that may depend on the target species and on the operating point of the previous sensor in the sensor array. For example, if the next sensor in the sensor array is the second sensor, the operating point of the second sensor may be set to higher selectivity mode relative to the first sensor's operating point. For example, the pulse height of the asymmetric oscillating field generated in the second sensor's filter may be set to a larger value than the pulse height of the first sensor's oscillating field.

The processed signal from the second sensor is compared to a predetermined threshold value associated with the operating point of the second sensor in step 1340. If the signal does not exceed the threshold value, the possible event may be classified as a false positive and the controller jumps back to step 1310 and may deactivate the second sensor. If the signal exceeds the threshold value, the controller determines if the most recently activated sensor is the last sensor in the sensor array in step 1350. If the most recently activated sensor is not the last sensor in the sensor array, the controller jumps back to step 1330 and activates the next sensor in the sensor array. For example, if the second sensor is the most recently activated sensor in a five-sensor array, the controller activates the third sensor in the sensor array and sets the third sensor's operating point to a predetermined operating point. The operating point of the third sensor may be set such that it has higher selectivity than the first or second sensor.

If the most recently activated sensor is the last sensor in the sensor array, then all the sensors in the sensor array have exceeded their respective thresholds and an alarm is registered in 1360.

The ability to control independently each sensor in the sensor array allows for a wide variety of operating modes that can be customized to a particular situation. For example, instead of operating the sensor array in a cascading sequence, the sensor array may be operated using groups of sensors within the sensor array.

In some embodiments, a sensor in the sensor array may be controlled to operate in a high sensitivity mode while the remaining sensors in the array are turned off to prolong battery life. When the high sensitivity sensor detects a possible event, the remaining sensors in the array may be turned on and set to a high selectivity operating point. Although the sensitivity of each sensor may decrease as selectivity increases, the activation of the remaining sensors in the array increases the effective flow of ions through the sensor array, thereby increasing the sensitivity of the array while operating in a high selectivity mode.

In some embodiments, the remaining sensors in the array may be controlled as a single group of sensors set to the same operating point, thereby making the group of sensors appear to be a single sensor with a large flow, or collection, cross-sectional area. For example, if the sensor array has nine FAIMS sensors with eight of the sensors controlled as a single group, the array will appear as a two-sensor array with the second sensor having an effective area that is eight times as large as a single FAIMS sensor. Operating the group of sensors at the same operating point may eliminate the need for separate electrode drive electronics, thereby reducing the cost and size of the sensor array.

Embodiments of the present invention comprise computer components and computer-implemented steps that will be apparent to those skilled in the art. For ease of exposition, not every step or element of the present invention is described herein as part of a computer system, but those skilled in the art will recognize that each step or element may have a corresponding computer system or software component. Such computer system and/or software components are therefore enabled by describing their corresponding steps or elements (that is, their functionality), and are within the scope of the present invention.

Having thus described at least illustrative embodiments of the invention, various modifications and improvements will readily occur to those skilled in the art and are intended to be within the scope of the invention. Accordingly, the foregoing description is by way of example only and is not intended as limiting. The invention is limited only as defined in the following claims and the equivalents thereto.

What is claimed is:

1. A method of operating a smart FAIMS sensor comprising: providing a FAIMS sensor comprising a filter for separating ionic species, the filter having at least two electrodes, each of the at least two electrodes having a first and second contact pad, each of the contact pads driven by a drive signal controlled by a controller and defining an operating point of the sensor, and a detector for collecting separated ionic species, the detector generating a detection signal in response to the collected ionic species; setting the operating point of the sensor to a first operating point; and setting the operating point of the sensor to a second operating point based on the detection signal.

2. The method of claim 1 further comprising registering an alarm when the detection signal generated at the second operating point exceeds a predetermined threshold associated with the second operating point.

3. The method of claim 1, wherein the second operating point is set when the detection signal generated at the first operating point exceeds a predetermined threshold associated with the first operating point.

4. The method of claim 1, wherein the operating point of the sensor is set by changing a drive voltage.

5. The method of claim 1, wherein the operating point of the sensor is set by changing a pulse height of an asymmetric oscillating signal applied to the plurality of electrodes.

6. The method of claim 1, wherein the first operating point corresponds to a high sensitivity operating mode.

7. The method of claim 1, wherein the second operating point corresponds to a high selectivity operating mode.

8. The method of claim 1, wherein the first operating point is set according to a threat condition in a deployed environment.

9. A method of operating a FAIMS sensor comprising: providing a FAIMS sensor with a filter for separating ionic species having at least two electrodes, each of the at least two electrodes having a first and second contact pad, each of the contact pads driven by a drive signal controlled by a controller and defining an operating point of the sensor, the sensor characterized by one or more operating parameters, the set of the one of more operating parameters defining an operating mode; placing the sensor into a first operating mode, the first operating mode characterized by a high sensitivity to a target species; dynamically switching to a second operating mode when the target species is detected at the first operating mode; and registering an alarm when the target species is detected at the second operating mode.

10. The method of claim 9 wherein the second operating mode is characterized by a lower sensitivity to the target species relative to the first operating mode and further characterized by a higher selectivity to the target species relative to the first operating mode.

11. The method of claim 9 wherein the one or more operating parameters includes a drive voltage, the drive voltage controlling an ion flow rate through a filter in the sensor.

12. The method of claim 11 wherein the step of dynamically switching comprises reducing the drive voltage.

13. The method of claim 9 wherein the one or more operating parameters includes a pulse height, the pulse height determining an amplitude of an asymmetric oscillating field generated in a filter in the sensor.

14. The method of claim 13 wherein the step of dynamically switching comprises increasing the pulse height.

* * * * *